United States Patent [19]

Cavalla et al.

[11] 4,197,239
[45] Apr. 8, 1980

[54] HEXAHYDROAZEPINE, PIPERIDINE AND PYRROLIDINE DERIVATIVES

[75] Inventors: John F. Cavalla, Isleworth; Alan C. White, Windsor; Robin G. Shepherd, Maidenhead, all of England

[73] Assignee: John Wyeth & Brother Limited, Maidenhead, England

[21] Appl. No.: 961,086

[22] Filed: Nov. 15, 1978

[30] Foreign Application Priority Data

Dec. 22, 1977 [GB] United Kingdom ............... 53370/77

[51] Int. Cl.² ........................................... C07D 223/10
[52] U.S. Cl. .................. 260/239.3 R; 260/326.5 FL; 260/239 B; 260/326.8; 424/244; 424/267; 424/274; 546/221; 546/236; 546/240
[58] Field of Search ............... 260/239.3 R, 326.5 FL; 546/221

[56] References Cited

FOREIGN PATENT DOCUMENTS 850777 7/1977 Belgium .......................... 236/326.5 M
1285025 8/1972 United Kingdom ............ 260/239.3 D

OTHER PUBLICATIONS

Duong et al., "Australian J. Chem." (1976) vol. 29, pp. 2651-2665.
Deslongschamps et al., "Canad. J. Chem." (1975) vol. 53, pp. 1682-1683.
Hullot et al., "Canad. J. Chem." (1976) vol. 54, pp. 1098-1104.
Kugita et al., "J. Med. Chem." (1965) vol. 8, pp. 313-316.
Cavalla et al., "J. Med. Chem." (1965) vol. 8, pp. 316-326.
Tamura, "J. Med. Chem." (1970) vol. 20, pp. 709-714.
Frostick et al., "J. Am. Chem. Soc." vol. 71 (1949) pp. 1350-1352.

*Primary Examiner*—Alan L. Rotman
*Assistant Examiner*—Robert T. Bond
*Attorney, Agent, or Firm*—Arthur E. Wilfond

[57] ABSTRACT

The invention concerns novel 2-oxo-hexahydroazepine, -piperidine and -pyrrolidine of formula I

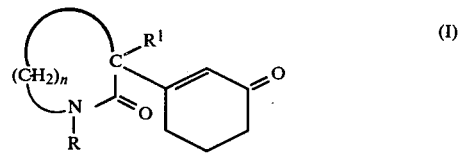

where n is 2,3 or 4, R is hydrogen, lower alkyl or aryl(-lower)alkyl and $R^1$ is lower alkyl. The compounds may be aromatized and the aromatized compounds converted to 3,3-disubstituted-hexahydroazepine, -piperidine and -pyrrolidine compounds having pharmacological activity, particularly analgesic activity.

5 Claims, No Drawings

HEXAHYDROAZEPINE, PIPERIDINE AND PYRROLIDINE DERIVATIVES

The invention relates to hexahydroazepine, piperidine and pyrrolidine derivatives. More particularly the invention relates to certain novel 2-oxo-hexahydroazepine, -piperidine and -pyrrolidine derivatives, to a novel process for preparing the novel derivatives and to the use of the novel derivatives in preparing 3,3-disubstituted-hexahydroazepine, -piperidine, and -pyrrolidine derivatives.

Various 3,3-disubstituted hexahydroazepines, -piperidines and -pyrrolidines are known to have pharmacological activity, particularly analgesic activity. For example, analgesic 2-unsubstituted-3,3-disubstituted-hexahydroazepines, such as meptazinol, are disclosed in U.K. Pat. No. 1,285,025. Profadol and related 3,3-disubstituted-pyrrolidines are described in J. Med. Chem. 1965, 8, 316 and Belgian Pat. No. 850,777 while myfadol and related 3,3-disubstituted-piperidines are described in J. Med. Chem, 1965, 8, 313. The known processes for preparing the 3,3-disubstituted-hexahydroazepines, -piperidines and -pyrrolidines are expensive and it is an object of the present invention to provide novel intermediates which may be easily prepared by a novel process from readily available starting materials and which can be converted into the desired 3,3-disubstituted -hexahydroazepines, -piperidines and pyrrolines such that the overall process for preparing the final products is generally more economic than the known processes.

The novel compounds provided by the invention are 2-oxo-hexahydroazepine, -piperidine and -pyrrolidine derivatives of the general formula (I)

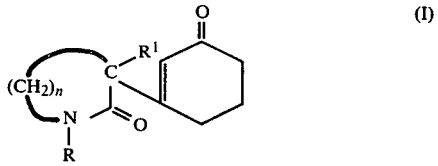

wherein n is 2, 3 or 4, R is hydrogen, lower alkyl or aryl(lower)alkyl, and $R^1$ is lower alkyl.

The term "lower" as used herein means that the radical referred to contains 1 to 6 carbon atoms. The radical preferably contains 1 to 4 carbon atoms. For example when R is lower alkyl, the radical may be, for example, methyl, ethyl, propyl or butyl. Similarly $R^1$ may be, for example, methyl, ethyl, propyl or butyl. When R is aryl(lower)alkyl, the radical is preferably a phenyl(lower)alkyl radical such as phenethyl or benzyl; the phenyl group may be substituted by, for example, one or more substituents such as halogen, alkoxy, trifluoromethyl or other substituents common in medicinal chemistry.

The compounds of general formula (I) may be converted by procedures described hereinafter to their aromatised derivatives of general formula (II)

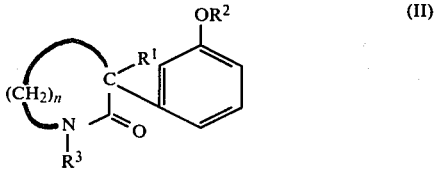

where n and $R^1$ are as defined above, $R^2$ is hydrogen, lower alkyl or aryl(lower)alkyl and $R^3$ is hydrogen, lower alkyl, aryl(lower)alkyl, lower alkenyl or lower alkynyl.

Where $R^3$ is lower alkenyl or lower alkynyl it is to be understood that the double or triple bond is not in the 1-position of the alkenyl or alkynyl radical; examples of suitable alkenyl and alkynyl radicals are allyl, propargyl, 3,3-dimethylallyl and 1-methyl-2-propynyl.

The compounds of general formula (II) may be prepared by aromatising and optionally O-(lower)alkylating or O-aryl(lower)alkylating the compounds of general formula (I) to give a compound of general formula (II) in which $R^3$ is hydrogen, lower alkyl or aryl(lower)alkyl and, if desired "N-alkylagting" a compound of general formula (II) in which $R^3$ is hydrogen to give a compound of general formula (II) in which $R^3$ is lower alkyl, aryl(lower)alkyl, lower alkenyl or lower alkynyl.

By "N-alkylating" is meant introducing onto the nitrogen atom of the heterocyclic ring a lower alkyl, aryl(lower)alkyl, lower alkenyl or lower alkynyl radical. A compound of formula (I) may be aromatised to a compound of formula (II) in which $R^2$ is hydrogen by treatment with cupric halide (e.g. cupric bromide or cupric chloride), in the presence or absence of lithium halide. The reaction may be carried out in a solvent such as tetrahydrofuran or, preferably, acetonitrile. Alternatively a compound of general formula (I) may be aromatised to a compound of general formula (II) by treatment with bromine, for example, in a solvent such as chloroform, methylene dichloride or carbon tetrachloride. Preferably not more than about 1 mole of bromine is used per mole of compound of general formula (I). Alternatively, a compound of formula (I) may be aromatised and O-(lower)alkylated to a compound of formula (II) in which $R^2$ is lower alkyl by treatment with bromine in presence of a lower alkanol (for example, in a solvent such as benzene, cyclohexane or acetonitrile) or by treatment with a brominating agent such as N-bromo-succinimide in, for example, a solvent such as chloroform, methylene dichloride or carbon tetrachloride containing a lower alkanol.

We have found that the compounds of general formula (I) can be prepared by a novel process from readily available starting materials. Accordingly in a further aspect the invention provides a process for preparing a compound of general formula (I) which comprises reacting a cyclohexane derivative of general formula (III)

where Q is a hydrolysable protecting group such as lower alkoxy (preferably methoxy, ethoxy or i-propyloxy), benzyloxy, trialkyl-, triaryl- or tri-aralkyl-silyloxy (e.g. trimethylsilyloxy) with an anion of a lactam of general formula (IV)

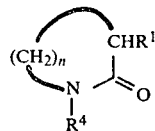

where n and $R^1$ are as defined above and $R^4$ is lower alkyl, aryl(lower)alkyl or trialkyl-, triaryl- or triaralkyl-silyl (e.g. trimethylsilyl) and subjecting the product to hydrolysis. The anion of the lactam of general formula (IV) may be prepared by reacting the lactam with a Grignard reagent (preferably isopropylmagnesium bromide) or with a dialkylamino magnesium halide e.g. bromomagnesiumdiisopropylamide.

The product of the reaction of the anion of the lactam of general formula (IV) and the cyclohexane derivative (III) is preferably not isolated but hydrolysed in situ to give the compound of general formula (I). If $R^4$ in the compound of general formula (IV) is a tri-alkyl-, tri-aryl- or tri-aralkyl-silyl group, this group is removed by hydrolysis to give a compound of general formula (I) in which R is hydrogen.

The compounds of formula (I) and their simple derivative of formula (II) are useful as intermediates for preparing pharmacologically active hexahydroazepine, piperidine and pyrrolidine derivatives. For example, compounds (I) can be aromatised (and optionally O-(lower)alkylated or O-aryl(lower)alkylated) as mentioned above to give compounds (II). The compounds of general formula (II) in which $R^3$ is hydrogen can also be "N-alkylated" as mentioned above; it is preferable to N-alkylate a compound in which $R^2$ is lower alkyl or aryl(lower)alkyl. Compounds of formula (II) in which $R^2$ is hydrogen can be O-(lower)alkylated or O-aryl(lower)alkylated to give compounds in which $R^2$ is lower alkyl or aryl(lower)alkyl. The 3,3-disubstituted compounds of formula (II) can be reduced to give a 2-unsubstituted-3,3-disubstituted-hexahydroazepine, -piperidine or -pyrrolidine derivative. An embodiment of this route for preparing 2-unsubstituted-3,3-disubstituted-hexahydroazepines is illustrated, by way of example, in the reaction scheme below:

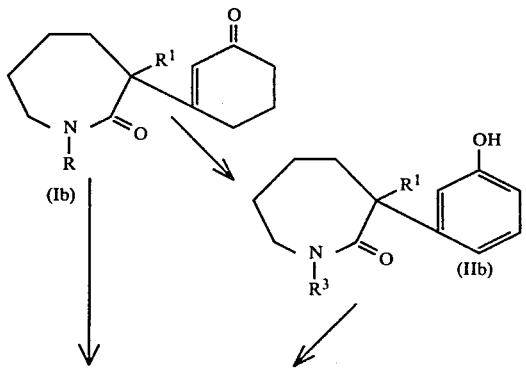

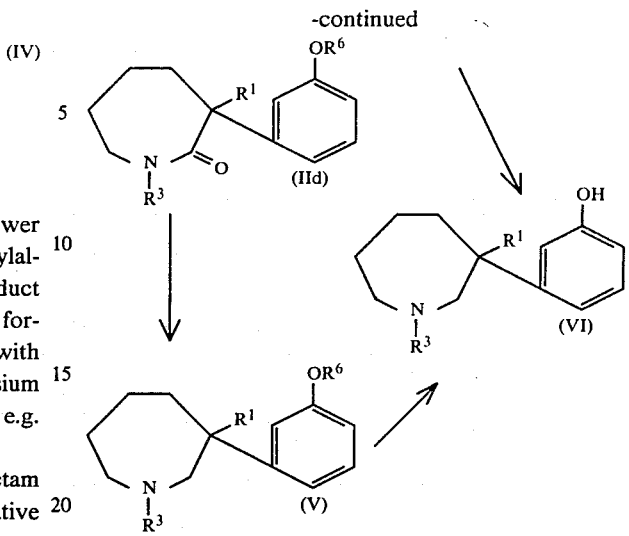

In this reaction scheme R, $R^1$ and $R^3$ have the meanings given above and $R^6$ is lower alkyl or aryl(lower)alkyl. Compound (Ib) can be aromatised to compound (IIb) by the procedure described above or alternatively compound (Ib) can be aromatised and O-(lower)alkylated to compounds (IIc) and (IId) respectively by the procedure described above. If desired compound (IIb) can be etherified to compound (IId) by treatment with a (lower) alkylating agent, e.g. dimethyl sulphate or with an aryl(lower)alkylating agent such as benzyl chloride. The compounds IIb and IId can be reduced to the compounds VII and VI respectively as disclosed in our U.K. Pat. No. 1,285,025. For example, the reduction can be carried out with a hydride transfer agent, e.g. lithium aluminium hydride. If desired compound VI can be converted to compound VII by ether cleavage, e.g. with hydrogen bromide or boron tribromide, as described in the above mentioned U.K. Pat. No. 1,285,025.

Compounds VI and VII Are disclosed in U.K. Pat. No. 1,285,025 as having pharmaceological activity, particularly analgesic activity. A particularly important analgesic compound is that of formula VII in which $R^3$ is methyl and $R^7$ is ethyl. This compound is meptazinol. The present invention provides a novel process for preparing such compounds in good yield from readily available starting materials. For example, the starting materials of formula V in which n is 4 are readily available derivatives of caprolactam.

The processes shown in the reaction scheme can be subject to various modifications. For example, the group in the 1-position of the intermediate compounds may be removed to give a N—H-derivative which may subsequently be alkylated, as for example, described in U.K. Pat. No. 1,285,025, to give a product having a different 1-substituent. Analogous reactions to those described above in connection with the Reaction Scheme and the modifications can be carried out with compounds I and II in which n is 2 or 3 to give analogous 2-unsubstituted-3,3-disubstituted-piperidines and -pyrrolidines having pharmacological activity such as profadol and related pyrrolidines described in J. Med. Chem., 1965, 8, 316 and Belgian Patent Specification No. 850777 and pyfadol and related piperidines described in J. Med. Chem., 1965, 8, 313.

The following examples illustrate the invention:

EXAMPLE 1

3-Ethyl-hexahydro-1-methyl-3-(3-oxocyclohexen-1-yl)-2H-azepin-2-one

A 2 molar solution of isopropylmagnesium bromide in ether (70 ml) was treated with 3-ethyl-hexahydro-1-methyl-2H-azepin-2-one (21.7 g, Aust. J. Chem. 1976, 29 2651) in THF (20 ml) and the mixture treated dropwise with diisopropylamine (19.6 ml) (exothermic). The reaction mixture was stirred for 2 hours then treated dropwise with 3-methoxy-2-cyclohexenone (12.6 g) in THF (20 ml). After stirring for 2 hours the reaction mixture was poured onto cold 2 N HCl (250 ml). After 10 minutes the mixture was extracted with dichloromethane (2×300 ml), the combined organic phases washed with saturated aqueous NaHCO₃ solution and dried (MgSO₄). Removal of the solvents under reduced pressure followed by distillation gave the title compound as a viscous oil (Bpt 155°–160° C./0.1 mm) (13 g). Redistillation (154°–158° C./0.07 mm) gave analytically pure material.

Analysis: Found: C, 72.4; H, 9.6; N, 5.4%. $C_{15}H_{23}NO_2$ requires C, 72.25; H, 9.3; N, 5.6%.

EXAMPLE 2

3-Ethyl-hexahydro-3-(3-hydroxyphenyl)-1-methyl-2H-azepin-2-one

A solution of crude 3-ethyl-hexahydro-1-methyl-3-(3-oxocyclohexen-1-yl)-2H-azepin-2-one (280.5 g) in methylene chloride (1.41) was stirred and treated with bromine (180 g) over 1.5 hours at 20°–25° C. with occasional water cooling. The reaction mixture was stirred at room temperature for two hours but TLC examination showed some starting material still present. Additional bromine (18 g) was added over ten minutes and the solution was stirred for a further one hour. TLC analysis detected no starting material so water (500 ml.) was added with cooling and the methylene chloride layer was washed with water (500 ml). The two water washes were combined, back-extracted woth methylene chloride (200 ml.) and the extract washed with water (100 ml.). The methylene chloride extracts were combined, evaporated to dryness, the fawn-coloured solid was triturated with ethyl acetate (250 ml), filtered, washed with ethyl acetate (50 ml) and dried in an air oven at 60° C. to give 244.7 g of title compound, m.p. 172°–175° C.

EXAMPLE 3

3-Ethyl-hexahydro-3-(3-hydroxyphenyl)-1-methyl-2H-azepine

A solution of 3-ethylhexahydro-3-(3-hydroxyphenyl)-1-methyl-2H-azepin-2-one (1.5 g) in dry tetrahydrofuran was added to a stirred suspension of aluminium lithium hydride (0.48 g) and heated under reflux for 5 hours. The reaction mixture was cooled and decomposed by the addition of water and the precipitate filtered. The precipitate was washed with tetrahydrofuran and the combined filtrate and washings evaporated to a solid. The solid was dissolved in water and ammonium chloride added. The precipitated oil was extracted with dichloromethane, dried over anhydrous magnesium sulphate and evaporated to leave a solid which was recrystallised from acetonitrile to give 0.91 g of the title compound, m.p. 127.5°–133° C., identical with material prepared by an alternative route described in U.K. Pat. No. 1,285,025.

We claim:

1. A compound of formula

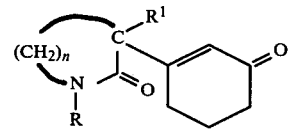

wherein n is 2,3 or 4, R is hydrogen, lower alkyl, phen(lower)alkyl or substituted phen(lower)alkyl, wherein the substituent is selected from halogen, lower alkoxy and trifluoromethyl and $R^1$ is lower alkyl.

2. A compound as claimed in claim 1 wherein R is hydrogen, lower alkyl or phen(lower)alkyl.

3. A compound as claimed in claim 1 wherein $R^1$ is ethyl.

4. A compound as claimed in claim 1 wherein n is 4.

5. A compound as claimed in claim 1 which is 3-ethyl-hexahydro-1-methyl-3-(3-oxocyclohexen-1-yl)-2H-azepin-2-one.

* * * * *

UNITED STATES PATENT OFFICE
CERTIFICATE OF CORRECTION

PATENT NO. : 4,197,239
DATED : April 8, 1980
INVENTOR(S) : J.F. Cavalla et al

It is certified that error appears in the above-identified patent and that said Letters Patent are hereby corrected as shown below:

Column 2, line 17 should read — "N-alkylating" — for " "N-alkylagting" ";

Column 4, line 34 should read — VI and V — for "VII and VI";

line 37 should read — V — for "VI";

line 38 should read —VI — for "VII";

line 41 should read — V and VI — for "VI and VII";

line 44 should read —VI — for "VII";

line 49 should read — IV — for "V".

Signed and Sealed this

Fourteenth Day of July 1981

[SEAL]

Attest:

Attesting Officer

GERALD J. MOSSINGHOFF

Commissioner of Patents and Trademarks